(12) United States Patent
Lloyd (10) Patent No.: US 9,080,193 B2
(45) Date of Patent: Jul. 14, 2015

(54) PREPARATION OF (3AS,7AR)-HEXAHYDROISOBENZOFURAN-1(3H)-ONE BY CATALYZED BIOLOGICAL RESOLUTION OF DIMETHYL CYCLOHEXANE-1,2-DICARBOXYLATE

(75) Inventor: Michael Charles Lloyd, Ely (GB)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/699,307

(22) PCT Filed: May 24, 2011

(86) PCT No.: PCT/US2011/037745
§ 371 (c)(1),
(2), (4) Date: Feb. 7, 2013

(87) PCT Pub. No.: WO2011/149938
PCT Pub. Date: Dec. 1, 2011

(65) Prior Publication Data
US 2013/0273618 A1    Oct. 17, 2013

Related U.S. Application Data

(60) Provisional application No. 61/347,487, filed on May 24, 2010.

(51) Int. Cl.
| C12P 17/04 | (2006.01) |
| C12P 7/62  | (2006.01) |
| C07D 307/88| (2006.01) |
| C12P 7/40  | (2006.01) |

(52) U.S. Cl.
CPC ............... *C12P 17/04* (2013.01); *C07D 307/88* (2013.01); *C12P 7/40* (2013.01); *C12P 7/62* (2013.01)

(58) Field of Classification Search
None
See application file for complete search history.

(56) References Cited

U.S. PATENT DOCUMENTS

| 4,879,392 A | 11/1989 | Brion et al. |
| 5,262,313 A | 11/1993 | Kitchell et al. |

FOREIGN PATENT DOCUMENTS

WO    WO 99/04015    * 1/1999

OTHER PUBLICATIONS

Sabbioni et al. J. Org. Chem. (1987) 52, 4565-4570.*
Borzilleri, R.M. et al., "Total synthesis of the unusual marine alkaloid (−)-Papuamine utilizing a novel imino ene reaction," J. Am. Chem. Soc. (1995) 117:10905-10913.
Brion, F. et al., "Stereoselective synthesis of a trans-octahydroindole derivative, precursor of trandolapril (RU 44 570), an inhibitor of angiotensin converting enzyme," Tetrahedron Lett. (1992) 33(34):4889-4892.
Jones, J.B., "1992 Alfred Bader Award Lecture. Probing the specificity of synthetically useful enzymes," Can. J. Chem. (1993) 71:1273-1282.
Renold, P. et al., "Comparison of the hydrolysis of cyclic meso-diesters with pig liver esterase (PLE) and rabbit liver esterase (RLE)," Biocatalysis and Biotransformation (1995) 12:37-46.
Toone, E.J. et al., "Active-site model for interpreting and predicting the specificity of pig liver esterase," J. Amer. Chem. Soc. (1990) 112:4946-4952.
Uppenberg, J. et al., "Crystallographic and molecular-modeling studies of lipase B from *Candida antarctica* reveal a sterospecificity pocket for secondary alcohols," Biochem. (1995) 34:16838-16851.
Uppenberg, J. et al., "The sequence, crystal structure determination and refinement of two crystal forms of lipase B from *Candida antarctica*," Structure (1994) 2:293-308.
International Search Report and Written Opinion for Application No. PCT/US2011/037745 dated Jan. 11, 2012 (9 pages).
Calero-Rueda, O. et al., "Study of a sterol esterase secreted by ophiostoma piceae: sequence, model and biochemical properties," Biochimica et Biophysica Acta—Proteins and Proteomics (2009) 1794(7):1099-1106.
European Patent Office Search Report for Application No. 11787246.5 dated Jul. 29, 2014.

* cited by examiner

*Primary Examiner* — Nashaat Nashed
(74) *Attorney, Agent, or Firm* — Lisa V. Mueller; Michael Best & Friedrich LLP (57) ABSTRACT

Processes for the synthesis of (3aS,7aR)-hexahydroisobenzofuran-1-(3H)-one, comprising comprising enzymatic hydrolysis of dimethyl cyclohexane-1,2-dicarboxylate to form (1S,2R)-2-(methoxycarbonyl) cyclohexanecarboxylic acid. The enzyme can be from a non-mammalian source.

12 Claims, 6 Drawing Sheets

FIG. 1

Seq Id No 1: Chirotech Esterase K

| | | | | | | | | | | | | | | |
|---|---|---|---|---|---|---|---|---|---|---|---|---|---|---|
|Met|Thr|Met|Ile|Thr|Pro|Ser|Ser|Ala|Met|Gly|Met|Ser|Ser|Thr|Phe|
|1| | |  |5| | | |10| | | | |15| |

Glu Phe Glu Arg Val Ile Thr Lys Ala Val Glu Asp Arg Val Ile Pro
            20                  25                  30

Gly Val Val Leu Leu Ala Glu Asn Ser Ser Gly Ser Tyr His Tyr Glu
            35                  40                  45

Lys Val Leu Gly Tyr Ser Ser Ile Glu Ala Gly Asn Glu Lys Lys Leu
    50                  55                  60

Glu Arg Asp Ser Val Phe Thr Phe Met Ser Met Thr Lys Phe Ile Thr
65                  70                  75                  80

Ala Ile Val Ala Met Gln Ala Val Glu Arg Gly Leu Trp Asp Leu Asp
            85                  90                  95

Ala Asp Val Ala Pro Leu Leu Pro Glu Leu Ala Ala Leu Pro Val Leu
            100                 105                 110

Lys Gly Phe Ser Asp Asp Gly Val Pro Glu Leu Val Pro Arg Glu Ser
        115                 120                 125

Ala Ile Thr Leu Arg Gln Leu Leu Ser His Thr Ser Gly Ala Ala Tyr
    130                 135                 140

Asp Phe Leu Ser Pro Asp Leu Ile Asn Tyr His Ala Trp Val Arg Lys
145                 150                 155                 160

Gln Pro Pro Ser Ala Gly Leu Glu Gln Pro Pro Ala Met Thr Val Ala
            165                 170                 175

Pro Pro Ser Val Glu Glu Arg Phe Arg Phe Pro Leu Val Phe Gln Pro
            180                 185                 190

Gly Gln Gly Trp Gln Tyr Gly Ser Ser Leu Asp Trp Val Gly Arg Leu
        195                 200                 205

Val Glu Arg Leu Asp Ala Lys Thr Gln Gly Lys Thr Glu Lys Glu Ala
    210                 215                 220

FIG. 1 (cont.)

```
Gly Thr Lys Leu Pro Ser Val Pro Leu Glu Glu Ile Val Ile Arg Asp
225                 230                 235                 240

Val Leu Thr Pro Leu Gly Leu Pro Ala Gly Ala Leu Thr Phe Ser Pro
            245                 250                 255

Glu Arg Tyr Pro Asp Val Phe Ala Arg Met Trp Pro Ser Leu Pro Val
            260                 265                 270

Arg Val Gly Asn Asn Gly Ala Leu Asp Gly Gly Pro Val Val His Gly
            275                 280                 285

Pro Ser Val Tyr Lys Lys Ala Pro Ala Ala Leu Gly Gly Gln Gly Met
            290                 295                 300

Tyr Gly Asp Met Pro Ser Phe Phe Lys Val Ala Leu Ser Ile Phe Arg
305                 310                 315                 320

Asp Asp Gly Lys Leu Leu Lys Pro Glu Ser Thr Lys Leu Phe Phe Glu
                325                 330                 335

Pro Gln Leu Ala Ser Glu Ala Ala His Ala Gly Ile Met His Gly Thr
            340                 345                 350

Glu Asn Ser Gly Trp Ile Thr Gly Asp Val Pro Asp Thr Lys Glu Tyr
            355                 360                 365

Asp Trp Ser Val Ala Gly Leu Leu Val Thr Gly Asp Ser His Pro Phe
    370                 375                 380

Arg Lys Arg Gly Ala Val Leu Trp Ala Gly Ala Ile Asn Leu Thr Trp
385                 390                 395                 400

Ile Ile Asp Lys Glu Ala Asp Val Cys Ala Val Phe Gly Ser Asn Tyr
                405                 410                 415

Gln Pro Pro Gly Asp Gln Gln Gly Lys Ala Leu Met Arg Gln Trp Glu
            420                 425                 430

Glu Phe Val Tyr Pro Gln Ala Lys Thr Ala Lys Leu
            435                 440
```

FIG. 1 (cont.)

Seq ID No 2: Chirotech Esterase N

```
Met Thr Met Ile Thr Pro Ser Ser Ala Met Gly Met Ser Ser Thr Phe
1               5                   10                  15

Glu Phe Glu Arg Val Ile Thr Lys Ala Val Glu Asp Arg Val Ile Pro
            20                  25                  30

Gly Val Val Leu Leu Ala Glu Asn Ser Ser Gly Ser Tyr His Tyr Glu
            35                  40                  45

Lys Val Leu Gly Tyr Ser Ser Ile Glu Ala Gly Asn Glu Lys Lys Leu
        50              55                  60

Glu Arg Asp Ser Val Phe Thr Phe Met Ser Met Thr Lys Phe Ile Thr
65                  70                  75                  80

Ala Ile Val Ala Met Gln Ala Val Glu Arg Gly Leu Trp Asp Leu Asp
                85                  90                  95

Ala Asp Val Ala Pro Leu Leu Pro Glu Leu Ala Ala Leu Pro Val Leu
            100                 105                 110

Lys Gly Phe Ser Asp Asp Gly Val Pro Glu Leu Val Pro Arg Glu Ser
            115                 120                 125

Ala Ile Thr Leu Arg Gln Leu Leu Ser His Thr Ser Gly Ala Ala Tyr
            130                 135                 140

Asp Phe Leu Ser Pro Asp Leu Ile Asn Tyr His Ala Trp Val Arg Lys
145                 150                 155                 160

Gln Pro Pro Ser Ala Gly Leu Glu Gln Pro Pro Ala Met Thr Val Ala
            165                 170                 175

Pro Pro Ser Val Glu Glu Arg Phe Arg Phe Pro Leu Val Phe Gln Pro
            180                 185                 190

Gly Gln Gly Trp Gln Tyr Gly Ser Ser Leu Asp Trp Val Gly Arg Leu
            195                 200                 205

Val Glu Arg Leu Asp Ala Lys Thr Gln Gly Lys Thr Glu Lys Glu Ala
            210                 215                 220

Gly Thr Lys Leu Pro Ser Val Pro Leu Glu Glu Ile Val Ile Arg Asp
225                 230                 235                 240
```

FIG. 1 (cont.)

```
Val Leu Thr Pro Leu Gly Leu Pro Ala Gly Ala Leu Thr Phe Ser Pro
                245                 250                 255

Glu Arg Tyr Pro Asp Val Phe Ala Arg Met Trp Pro Ser Leu Pro Val
                260                 265                 270

Arg Val Gly Asn Asn Gly Ala Leu Asp Gly Gly Pro Val Val His Gly
            275                 280                 285

Pro Ser Val Tyr Lys Lys Ala Pro Ala Ala Leu Gly Gly Gln Gly Met
            290                 295                 300

Tyr Gly Asp Met Pro Ser Phe Phe Lys Val Ala Leu Ser Ile Phe Arg
305                 310                 315                 320

Asp Asp Gly Lys Leu Leu Lys Pro Glu Ser Thr Lys Leu Phe Phe Glu
                325                 330                 335

Pro Gln Leu Ala Ser Lys Ala Ala His Ala Gly Ile Met His Gly Thr
                340                 345                 350

Glu Asn Ser Gly Trp Ile Thr Gly Asp Val Pro Asp Thr Lys Glu Tyr
            355                 360                 365

Asp Trp Ser Val Ala Gly Leu Leu Val Thr Gly Asp Ser His Pro Phe
            370                 375                 380

Arg Lys Arg Gly Ala Val Leu Trp Ala Gly Ala Phe Asn Leu Thr Trp
385                 390                 395                 400

Ile Ile Asp Lys Glu Ala Asp Val Cys Ala Val Phe Gly Ser Asn Tyr
                405                 410                 415

Gln Pro Pro Gly Asp Gln Gln Gly Lys Ala Leu Met Arg Gln Trp Glu
                420                 425                 430

Glu Phe Val Tyr Pro Gln Ala Lys Thr Ala Lys Leu
            435                 440
```

Seq ID No 3: Candida antartica lipase    FIG. 1 (cont.)

```
Leu Pro Ser Gly Ser Asp Pro Ala Phe Ser Gln Pro Lys Ser Val Leu
 1               5                  10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Thr Gln Leu Gly Tyr Thr Pro Cys
        50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
                100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
            130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
            195                 200                 205

Asn Val Gln Ala Gln Ala Val Cys Gly Pro Leu Phe Val Ile Asp His
            210                 215                 220

Ala Gly Ser Leu Thr Ser Gln Phe Ser Tyr Val Val Gly Arg Ser Ala
225                 230                 235                 240
```

FIG. 1 (cont.)

```
Leu Arg Ser Thr Thr Gly Gln Ala Arg Ser Ala Asp Tyr Gly Ile Thr
            245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
        290                 295                 300

Ala Val Gly Lys Arg Thr Cys Ser Gly Ile Val Thr Pro
305                 310                 315
```

PREPARATION OF (3AS,7AR)-HEXAHYDROISOBENZOFURAN-1(3H)-ONE BY CATALYZED BIOLOGICAL RESOLUTION OF DIMETHYL CYCLOHEXANE-1,2-DICARBOXYLATE

CROSS-REFERENCE TO RELATED APPLICATION(S)

This is a U.S. national stage entry of International Patent Application No. PCT/US2011/037745, filed on May 24, 2011, which claims priority to U.S. Provisional Patent Application No. 61/347,487, filed on May 24, 2010.

The instant application contains a Sequence Listing which has been submitted via EFS-Web and is hereby incorporated by reference in its entirety.

INTRODUCTION

The present application relates to processes for preparing (3aS,7aR)-hexahydroisobenzofuran-1(3H)-one 1, an intermediate in the synthesis of (2S,3aR,7aS)-benzyloctahydro-1H-indole-2-carboxylate hydrochloride.

A prior synthetic process utilizes pig liver esterase. It would be desirable to replace the pig liver esterase in this process with a non-mammalian derived enzyme. Furthermore, the (1R,2S)-2-(methoxycarbonyl)cyclohexane carboxylic acid 4 obtained from this pig liver esterase biological resolution has only 80% e.e. which means that a salt upgrade is required to produce material of >98% e.e. An alternative enzyme that would deliver a higher e.e. product, thus eliminating the need for a salt upgrade step in the process, would be simpler and lower the production costs. Furthermore, the use of an immobilized enzyme would facilitate the recycling of biocatalyst.

Various patents and journal articles disclose processes for the preparation of optically enriched 2-(methoxycarbonyl) cyclohexanecarboxylic acid. Pig liver esterase catalyzed biological resolution of dimethyl cyclohexane-1,2-dicarboxylate 2 is described by: U.S. Pat. No. 4,879,392; F. Brion et al., "Stereoselective Synthesis of a trans-Octahydroindole Derivative, Precursor of Trandolapril, an Inhibitor of Angiotensin Converting Enzyme," *Tetrahedron Letters*, Vol. 33, No. 34, pages 4889-4892, 1992; R. M. Borzilleri et al., "Total Synthesis of the Unusual Marine Alkaloid (−)-Papuamine Utilizing a Novel Imino Ene Reaction," *Journal of the American Chemical Society*, Vol. 117, pages 10905-10913, 1995.

SUMMARY

An aspect of the present application provides processes for the synthesis of (3aS,7aR)-hexahydroisobenzofuran-1-(3H)-one of 1. In an aspect, the present application provides processes for preparing (1S,2R)-2-(methoxycarbonyl) cyclohexanecarboxylic acid 3, an intermediate in the preparation of 1.

DETAILED DESCRIPTION

An aspect of the present application provides processes for the synthesis of (1S,2R)-2-(methoxycarbonyl) cyclohexanecarboxylic acid 3, comprising enzymatic hydrolysis of dimethyl cyclohexane-1,2-dicarboxylate 2.

An aspect of the present application provides processes for preparing (3aS,7aR)-hexahydroisobenzofuran-1-(3H)-one 1, comprising reductive cyclization of 3.

An aspect of the present application provides processes wherein an enzymatic hydrolysis uses an immobilized enzyme formulation.

An aspect of the present application provides processes using an immobilized enzyme formulation having a matrix that is cross-linked by, for example, treatment with glutaraldehyde.

Figure 1:
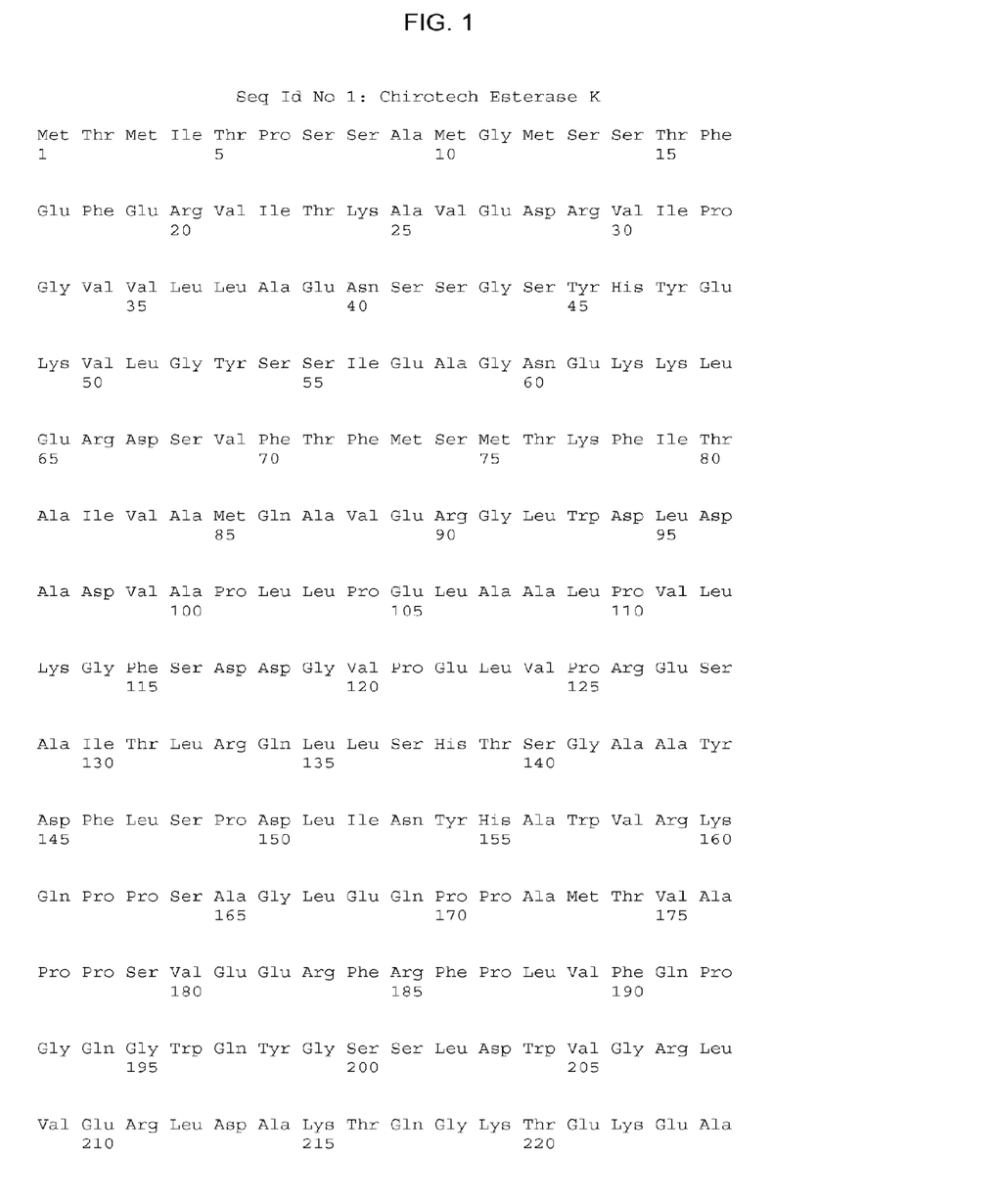
FIG. 1 is a listing of the sequences for three enzymes, identified as Chirotech Esterase K, Chirotech Esterase N, and *Candida Antarctica* Lipase.

Aspects of the present application provide processes wherein an enzymatic hydrolysis uses an enzyme such as, but not limited to, any of the lipases Chirotech Esterase K or Chirotech Esterase N (their sequence listings, as well as the listing for a useful native CAL-B enzyme, being shown in FIG. 1), Novozym™ 435, NZL-107 LYO, and 42044 from Novozymes A/S, ICR-110 CALB from Codexis, CV-CALB and CALB-Y from Chiralvision, and the serine esterase cutinase. Mixtures of enzymes are also useful. The enzymes are useful in any physical forms, such as their solutions and as their dispersions in resins that immobilize the enzymes.

Among the useful enzymes are those derived from *Candida antarctica*, including those described by: J. Uppenberg et al., "The Sequence, Crystal Structure Determination and Refinement of Two Crystal Forms of Lipase B from *Candida Antarctica,*" *Structure*, Vol. 2(4), pages 293-308, 1994; and J. Uppenberg et al., "Crystallographic and Molecular-Modeling Studies of Lipase B from *Candida Antarctica* Reveal a Stereospecifity Pocket for Secondary Alcohols," *Biochemistry*, Vol. 34(51), pages 16838-16851, 1995.

Embodiments of the present application provide processes wherein an enzymatic hydrolysis uses Novozym™ 435 enzyme.

Embodiments of the present application provide processes wherein a substrate concentration is about 10-200 g/L.

Embodiments of the present application provide processes wherein a substrate concentration is at least about 75 g/L.

Embodiments of the present application provide processes wherein enzyme loading is about 1% to about 20%, with respect to the weight of substrate.

Embodiments of the present application provide processes wherein enzyme loading is less than about 10%, with respect to the weight of substrate.

Embodiments of the present application provide processes wherein enzymatic hydrolysis temperatures are in the range of about 10° C. to about 50° C.

Embodiments of the present application provide processes wherein enzymatic hydrolysis temperature is about 40° C.

Embodiments of the present application provide processes wherein an enzymatic hydrolysis pH is in the range of about 6 to about 9.

Embodiments of the present application provide processes wherein an enzymatic hydrolysis pH is in the range of about 7 to about 8.

An aspect of the present application provides processes wherein a hydrolysis enzyme is added directly to a reaction vessel, recovered by filtration after the biological resolution is complete, then is washed with fresh buffer and added to a fresh batch of substrate/buffer.

In embodiments, a fresh buffer is a phosphate buffer.

An aspect of the present application provides processes wherein a hydrolysis enzyme is contained within a column reactor, a biological resolution batch is continuously circulated through the column, after the biological resolution is complete the column is washed with fresh buffer, and the next batch of substrate/buffer can be circulated through the column.

In embodiments, a fresh buffer is a phosphate buffer.

An aspect of the present application provides processes wherein reductive cyclization of (1S,2R)-2-(methoxycarbonyl) cyclohexanecarboxylic acid (3) utilizes a $C_1$-$C_6$ alkyl chloroformate, followed by reduction with a boron hydride.

An aspect of the present application provides processes wherein a $C_1$-$C_6$ alkylchloroformate is ethyl chloroformate.

An aspect of the present application provides processes wherein a boron hydride is sodium borohydride.

The enzyme Novozym™ 435 is used herein to exemplify enzyme hydrolysis processes. This product is an immobilized granulate *Candida antarctica* lipase B having a macroporous acrylic resin polymeric matrix. Novozym 435 is not mammalian-derived and can yield products with e.e. of 98%, thus eliminating the need for a salt upgrade step in the process. This enzyme source has been recycled at least eight times, in experiments.

In embodiments of this application, (3aS,7aR)-hexahydroisobenzofuran-1-(3H)-one (1) is prepared by initial treatment of (1S,2R)-2-(methoxycarbonyl) cyclohexanecarboxylic acid (3) with ethyl chloroformate, to yield the intermediate mixed anhydride, and a subsequent reduction with sodium borohydride yields the corresponding hydroxy ester, which cyclizes in situ to produce the desired cis-lactone product.

Novozym™ 435 catalyzed biological resolution of dimethyl cyclohexane-1,2-dicarboxylate (2) produces (1S,2R)- rather than (1R,2S)-2-(methoxycarbonyl) cyclohexanecarboxylic acid. However, reduction of the acid moiety, rather than the ester moiety, in the following synthetic step leads to cis-lactone with the same stereochemistry as that obtained using pig liver esterase. Furthermore, biological resolution yields product of significantly higher e.e. than is known in the art (98% vs. 80%). Novozym™ 435 is an immobilized enzyme preparation, which allows the biocatalyst to be recycled. A non-mammalian enzyme is amenable to recycling and delivers higher e.e. product. This eliminates the requirement for a salt upgrade to improve product e.e.

DEFINITIONS

The following definitions are used in connection with the compounds of the present application unless the context indicates otherwise. In general, the number of carbon atoms present in a given group is designated "$C_x$-$C_y$," where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions and the like.

"Alkyl" refers to a hydrocarbon chain that may be a straight chain or branched chain, containing the indicated number of carbon atoms. In the absence of any numerical designation, "alkyl" is a chain, straight or branched, having 1 to 6 (inclusive) carbon atoms in it. Examples of $C_1$-$C_6$ alkyl groups include, but are not limited to, methyl, ethyl, propyl, butyl, pentyl, hexyl, isopropyl, isobutyl, sec-butyl, tert-butyl, isopentyl, neopentyl, and isohexyl.

"$C_1$-$C_6$ alkyl chloroformate" refers to a compound of the formula R—O—C(O)—Cl, where R is a $C_1$-$C_6$ alkyl group.

A "boron hydride" is a reducing agent, which will reduce an acid in the presence of an ester. Examples of these include but are not limited to sodium borohydride, zinc borohydride, diborane, $BH_3$/THF, and 9-BBN.

The term "e.e." means the enantiomeric excess of a substance, which is defined as the absolute difference between the mole fractions of each enantiomer and expressed as a percentage.

The material sold as Celite™ is flux-calcined diatomaceous earth. Celite™ is a registered trademark of World Minerals Inc. GC is gas chromatography. NMR is nuclear magnetic resonance spectroscopy. MTBE is methyl t-butyl ether or 2-methoxy-2-methylpropane. Novozym™ NZL-107 LYO is a lipase of fungal origin. Novozym™ 435 is an immobilized form of lipase B from *Candida antarctica*. Novozym™ is a registered trademark of Novozymes A/S, Novo Industri A/S Bagsvaerd DK-2880 Denmark. PLE is pig liver esterase. Chirotech Esterase K 310-903 catalyses the stereoselective hydrolysis of esters, especially carboxylate esters. Chirotech Esterase K 310-903 is a recombinant enzyme originally isolated from the fungus *Ophiostoma*. Chirotech Esterase N 310-902 catalyses the stereoselective hydrolysis of esters, especially carboxylate esters, and is a recombinant enzyme originally isolated from the fungus *Ophiostoma*.

Certain aspects of the process of the present application will be explained in more detail with reference to the following Examples 1 and 2, which are provided for purposes of illustration only and should not be construed as limiting the scope of the disclosure in any manner.

EXAMPLE 1

Preparation of (1S,2R)-2-(methoxycarbonyl) cyclohexanecarboxylic acid (3)

Into a 100 mL jacketed vessel was placed dimethyl cyclohexane-1,2-dicarboxylate (2, 4 g, 20 mmol) and 39 mL of 0.1M potassium phosphate buffer, pH 8. The mixture was continuously stirred at 40° C. and Novozym™ 435 (320 mg) was added. Stirring was continued at 40° C. for 43 hours and pH was maintained at 8 by addition of 2M NaOH solution. A sample from the reaction was analyzed by GC to confirm that less than 5% of the starting material remained. The reaction mixture was filtered to remove the enzyme and the filtrate was extracted with toluene (20 mL) to remove any residual starting material. The pH of the aqueous phase was readjusted to 3.5 with 2M HCl and it was extracted with 2×50 mL of MTBE. The combined extracts were dried over magnesium sulfate and concentrated under reduced pressure to yield 3.2 g (86%) of (1S,2R)-2-(methoxycarbonyl) cyclohexane carboxylic acid (3) as a colorless oil with e.e.=98%. The isolated enzyme is washed with fresh buffer for reuse with a second batch of substrate/buffer.

$^1$H-NMR (d$_6$-DMSO): 12.17 (brs; 1H), 3.57 (s; 3H), 2.82-2.72 (m; 2H), 1.97-1.79 (m; 2H), 1.79-1.59 (m; 2H), 1.48-1.26 (m; 4H); $^{13}$C-NMR (d$_6$-DMSO): 174.61, 173.62, 51.16, 41.63, 25.96, 25.60, 23.34, 23.17.

The GC analytical conditions are: Chirasil Dex-CB 25 m×0.25 mm column; helium carrier gas, 20 psi; oven program is 140° C. hold for 30 minutes, then 5° C./minute to 200° C. and hold for 5 minutes (about 47 minutes run time); detector and injector temperatures 200° C.; retention times 36.99 minutes for 2-(methoxycarbonyl) cyclohexanecarboxylic acid (1S,2R) and 37.28 minutes for 2-(methoxycarbonyl) cyclohexanecarboxylic acid (1R,2S).

EXAMPLE 2

Preparation of (3aS,7aR)-hexahydroisobenzofuran-1-(3H)-one (1)

Into a 25 mL jacketed vessel cooled to below 0° C. was placed a solution of (1S,2R)-2-(methoxycarbonyl) cyclohexane carboxylic acid (3, 880 mg, 4.72 mmol) and triethylamine 659 μL, 4.72 mmol) in THF (6.6 mL). A solution of ethyl chloroformate (512 μL, 4.72 mmol) in 1.2 mL of THF was added slowly over a few minutes and the resulting mixture was stirred for 30 minutes. The precipitated triethylamine hydrochloride salt was removed by filtration and the filtrate was added drop-wise to a suspension of sodium borohydride in 4.6 mL of water at 12° C. After the addition was complete, the reaction mixture was stirred at 20° C. for a further 3.5 hours. The reaction mixture was then cooled to below 10° C., acidified to pH 4 with 2M HCl solution, and extracted with 2×15 mL of dichloromethane. The combined organic extracts were dried over magnesium sulfate and solvent was removed under reduced pressure, to yield 450 mg of a colorless oil. The material was purified by short path distillation to yield 170 mg of colorless oil with e.e.=98% and $[\alpha]_D^{20}$=−39.3° (c 1, methanol).

COMPARATIVE EXAMPLE

Preparation of (1R,2S)-2-(methoxycarbonyl)-cyclohexane carboxylic acid

Into a 2-L jacketed vessel set at 30° C. was placed dimethyl cyclohexane-1,2-dicarboxylate (2, 84.6 g, 0.42 mol) and 900 mL of 0.1M potassium phosphate buffer, pH 8. The mixture was continuously stirred at 30° C. and PLE (600 mg, 10200 units) was added. The mixture was stirred for 91 hours and the pH was maintained at 8 by addition of 5M NaOH solution. An aliquot from the mixture was analyzed by GC to confirm that residual starting material was less than 5%. The reaction mixture was then filtered through a Celite™ bed and the filtrate was extracted with 250 mL MTBE to remove residual starting material. The aqueous phase was then acidified to pH 4 with concentrated HCl and extracted with 3×500 mL MTBE. The combined extracts were dried over magnesium sulfate and solvent was removed under reduced pressure, to yield 69.28 g (88% yield) of (1R,2S)-2-(methoxycarbonyl) cyclohexane carboxylic acid (4) as a colorless oil with e.e.=79%.

While particular embodiments of the present application have been illustrated and described, it will be apparent to those skilled in the art that various changes and modifications can be made, without departing from the spirit and scope of the disclosure. It is therefore intended to cover in the appended claims all such changes and modifications that are within the scope of this disclosure.

The invention claimed is:

1. A process for preparing (3aS,7aR)-hexahydroisobenzofuran-1(3H)-one, comprising hydrolyzing dimethyl cyclohexane-1,2-dicarboxylate in the presence of an enzyme that is not derived from a mammalian source, wherein the enzyme is selected from the group consisting of SEQ ID NO:1, SEQ ID NO:2, and SEQ ID NO:3.

2. The process of claim 1, wherein the enzyme is SEQ ID NO:3.

3. The process of claim 1, wherein the enzyme is SEQ ID NO:1 or SEQ ID NO:2.

4. The process of claim 1 where the enzyme is in immobilized form.

5. The process of claim 1, wherein (3aS,7aR)-hexahydroisobenzofuran-1(3H)-one is prepared with an e.e. at least 95%.

6. The process of claim 1, wherein (3aS,7aR)-hexahydroisobenzofuran-1(3H)-one is prepared with an e.e. at least 98%.

7. A process for preparing (1S,2R)-2-(methoxycarbonyl)cyclohexanecarboxylic acid, comprising hydrolyzing dimethyl cyclohexane-1,2-dicarboxylate in the presence of an enzyme that is not derived from a mammalian source, wherein the enzyme is selected from the group consisting of SEQ ID NO:1, SEQ ID NO:2, and SEQ ID NO:3.

8. The process of claim 7, wherein the enzyme is SEQ ID NO:3.

9. The process of claim 7, wherein the enzyme is SEQ ID NO:1 or SEQ ID NO:2.

10. The process of claim 7 where the enzyme is in immobilized form.

11. The process of claim 7, wherein (1S,2R)-2-(methoxycarbonyl)cyclohexanecarboxylic acid is prepared with an e.e. at least 95%.

12. The process of claim 1, wherein (1S,2R)-2-(methoxycarbonyl)cyclohexanecarboxylic acid is prepared with an e.e. at least 98%.

* * * * *

SEQUENCE LISTING

<160> NUMBER OF SEQ ID NOS: 3

<210> SEQ ID NO 1
<211> LENGTH: 444

<212> TYPE: PRT
<213> ORGANISM: Ophiostoma

<400> SEQUENCE: 1

```
Met Thr Met Ile Thr Pro Ser Ala Met Gly Met Ser Ser Thr Phe
1               5                  10                  15

Glu Phe Glu Arg Val Ile Thr Lys Ala Val Glu Asp Arg Val Ile Pro
            20                  25                  30

Gly Val Val Leu Leu Ala Glu Asn Ser Ser Gly Ser Tyr His Tyr Glu
                35                  40                  45

Lys Val Leu Gly Tyr Ser Ser Ile Glu Ala Gly Asn Glu Lys Lys Leu
    50                  55                  60

Glu Arg Asp Ser Val Phe Thr Phe Met Ser Met Thr Lys Phe Ile Thr
65                  70                  75                  80

Ala Ile Val Ala Met Gln Ala Val Glu Arg Gly Leu Trp Asp Leu Asp
                85                  90                  95

Ala Asp Val Ala Pro Leu Leu Pro Glu Leu Ala Leu Pro Val Leu
                100                 105                 110

Lys Gly Phe Ser Asp Asp Gly Val Pro Glu Leu Val Pro Arg Glu Ser
            115                 120                 125

Ala Ile Thr Leu Arg Gln Leu Leu Ser His Thr Ser Gly Ala Ala Tyr
    130                 135                 140

Asp Phe Leu Ser Pro Asp Leu Ile Asn Tyr His Ala Trp Val Arg Lys
145                 150                 155                 160

Gln Pro Pro Ser Ala Gly Leu Glu Gln Pro Ala Met Thr Val Ala
                165                 170                 175

Pro Pro Ser Val Glu Glu Arg Phe Arg Phe Pro Leu Val Phe Gln Pro
            180                 185                 190

Gly Gln Gly Trp Gln Tyr Gly Ser Ser Leu Asp Trp Val Gly Arg Leu
        195                 200                 205

Val Glu Arg Leu Asp Ala Lys Thr Gln Gly Lys Thr Glu Lys Glu Ala
    210                 215                 220

Gly Thr Lys Leu Pro Ser Val Pro Leu Glu Glu Ile Val Ile Arg Asp
225                 230                 235                 240

Val Leu Thr Pro Leu Gly Leu Pro Ala Gly Ala Leu Thr Phe Ser Pro
                245                 250                 255

Glu Arg Tyr Pro Asp Val Phe Ala Arg Met Trp Pro Ser Leu Pro Val
            260                 265                 270

Arg Val Gly Asn Asn Gly Ala Leu Asp Gly Gly Pro Val Val His Gly
        275                 280                 285

Pro Ser Val Tyr Lys Lys Ala Pro Ala Ala Leu Gly Gln Gly Met
    290                 295                 300

Tyr Gly Asp Met Pro Ser Phe Phe Lys Val Ala Leu Ser Ile Phe Arg
305                 310                 315                 320

Asp Asp Gly Lys Leu Leu Lys Pro Glu Ser Thr Lys Leu Phe Phe Glu
                325                 330                 335

Pro Gln Leu Ala Ser Glu Ala Ala His Ala Gly Ile Met His Gly Thr
            340                 345                 350

Glu Asn Ser Gly Trp Ile Thr Gly Asp Val Pro Asp Thr Lys Glu Tyr
        355                 360                 365

Asp Trp Ser Val Ala Gly Leu Leu Val Thr Gly Asp Ser His Pro Phe
    370                 375                 380

Arg Lys Arg Gly Ala Val Leu Trp Ala Gly Ala Ile Asn Leu Thr Trp
385                 390                 395                 400
```

```
Ile Ile Asp Lys Glu Ala Asp Val Cys Ala Val Phe Gly Ser Asn Tyr
            405                 410                 415

Gln Pro Pro Gly Asp Gln Gly Lys Ala Leu Met Arg Gln Trp Glu
            420                 425                 430

Glu Phe Val Tyr Pro Gln Ala Lys Thr Ala Lys Leu
            435                 440

<210> SEQ ID NO 2
<211> LENGTH: 444
<212> TYPE: PRT
<213> ORGANISM: Ophistoma

<400> SEQUENCE: 2

Met Thr Met Ile Thr Pro Ser Ser Ala Met Gly Met Ser Ser Thr Phe
1               5                   10                  15

Glu Phe Glu Arg Val Ile Thr Lys Ala Val Glu Asp Arg Val Ile Pro
            20                  25                  30

Gly Val Val Leu Leu Ala Glu Asn Ser Ser Gly Ser Tyr His Tyr Glu
            35                  40                  45

Lys Val Leu Gly Tyr Ser Ser Ile Glu Ala Gly Asn Glu Lys Lys Leu
50                  55                  60

Glu Arg Asp Ser Val Phe Thr Phe Met Ser Met Thr Lys Phe Ile Thr
65                  70                  75                  80

Ala Ile Val Ala Met Gln Ala Val Glu Arg Gly Leu Trp Asp Leu Asp
                85                  90                  95

Ala Asp Val Ala Pro Leu Leu Pro Glu Leu Ala Ala Leu Pro Val Leu
            100                 105                 110

Lys Gly Phe Ser Asp Asp Gly Val Pro Glu Leu Val Pro Arg Glu Ser
            115                 120                 125

Ala Ile Thr Leu Arg Gln Leu Leu Ser His Thr Ser Gly Ala Ala Tyr
            130                 135                 140

Asp Phe Leu Ser Pro Asp Leu Ile Asn Tyr His Ala Trp Val Arg Lys
145                 150                 155                 160

Gln Pro Pro Ser Ala Gly Leu Glu Gln Pro Ala Met Thr Val Ala
            165                 170                 175

Pro Pro Ser Val Glu Glu Arg Phe Arg Phe Pro Leu Val Phe Gln Pro
            180                 185                 190

Gly Gln Gly Trp Gln Tyr Gly Ser Ser Leu Asp Trp Val Gly Arg Leu
            195                 200                 205

Val Glu Arg Leu Asp Ala Lys Thr Gln Gly Lys Thr Glu Lys Glu Ala
            210                 215                 220

Gly Thr Lys Leu Pro Ser Val Pro Leu Glu Glu Ile Val Ile Arg Asp
225                 230                 235                 240

Val Leu Thr Pro Leu Gly Leu Pro Ala Gly Ala Leu Thr Phe Ser Pro
            245                 250                 255

Glu Arg Tyr Pro Asp Val Phe Ala Arg Met Trp Pro Ser Leu Pro Val
            260                 265                 270

Arg Val Gly Asn Asn Gly Ala Leu Asp Gly Gly Pro Val Val His Gly
            275                 280                 285

Pro Ser Val Tyr Lys Lys Ala Pro Ala Ala Leu Gly Gly Gln Gly Met
            290                 295                 300

Tyr Gly Asp Met Pro Ser Phe Phe Lys Val Ala Leu Ser Ile Phe Arg
305                 310                 315                 320

Asp Asp Gly Lys Leu Leu Lys Pro Glu Ser Thr Lys Leu Phe Phe Glu
```

```
                    325                 330                 335
Pro Gln Leu Ala Ser Lys Ala His Ala Gly Ile Met His Gly Thr
                340                 345                 350

Glu Asn Ser Gly Trp Ile Thr Gly Asp Val Pro Asp Thr Lys Glu Tyr
                355                 360                 365

Asp Trp Ser Val Ala Gly Leu Val Thr Gly Asp Ser His Pro Phe
370                 375                 380

Arg Lys Arg Gly Ala Val Leu Trp Ala Gly Ala Phe Asn Leu Thr Trp
385                 390                 395                 400

Ile Ile Asp Lys Glu Ala Asp Val Cys Ala Val Phe Gly Ser Asn Tyr
                405                 410                 415

Gln Pro Pro Gly Asp Gln Gly Lys Ala Leu Met Arg Gln Trp Glu
                420                 425                 430

Glu Phe Val Tyr Pro Gln Ala Lys Thr Ala Lys Leu
                435                 440

<210> SEQ ID NO 3
<211> LENGTH: 317
<212> TYPE: PRT
<213> ORGANISM: Candida antartica

<400> SEQUENCE: 3

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Thr Gln Leu Gly Tyr Thr Pro Cys
50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
                100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
                195                 200                 205

Asn Val Gln Ala Gln Ala Val Cys Gly Pro Leu Phe Val Ile Asp His
                210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255
```

-continued

```
Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
        275                 280                 285

Pro Lys Gln Asn Cys Glu Pro Asp Leu Met Pro Tyr Ala Arg Pro Phe
        290                 295                 300

Ala Val Gly Lys Arg Thr Cys Ser Gly Ile Val Thr Pro
305                 310                 315
```